United States Patent [19]
Brooks

[11] Patent Number: 5,846,556
[45] Date of Patent: Dec. 8, 1998

[54] INHALANT FOR REDUCING STRESS AND METHOD OF USE

[76] Inventor: Bradley S. Brooks, 12222 E. Cove Cir., Orlando, Fla. 32826

[21] Appl. No.: 664,127

[22] Filed: Jun. 14, 1996

[51] Int. Cl.$^6$ .............................. A61F 13/00; A61K 9/00
[52] U.S. Cl. ........................... 424/434; 424/422; 424/400
[58] Field of Search ............................................. 424/434

[56] References Cited

U.S. PATENT DOCUMENTS

| | | |
|---|---|---|
| 87,319 | 2/1869 | Barker . |
| 123,714 | 2/1872 | Martin . |
| 283,800 | 8/1883 | Mayo . |
| 320,150 | 6/1885 | Mayo . |
| 3,192,106 | 6/1965 | Bracken et al. . |

FOREIGN PATENT DOCUMENTS

| | | |
|---|---|---|
| 646989 | 6/1937 | Germany . |
| 967930 | 8/1964 | United Kingdom . |

OTHER PUBLICATIONS

Sundin et al., "Anxiolyhc effects of low dosage . . . " Southern Medical Journal 74(12):1489–1492, 1981.
Aldrich® Chemical Company mail–order catalog, 1992, pp. 938–939, Aldrich Chemical Company, Milwaukee, WI.

*Primary Examiner*—Lynette F. Smith
*Attorney, Agent, or Firm*—Allen, Dyer, Doppelt, Milbrath & Gilchrist, P.A.

[57] ABSTRACT

An inhalant composition is provided that includes nitrogen, oxygen, an inert gas, carbon dioxide, and an anaesthetic agent present in a proportion insufficient to produce anaesthesia. Preferably the inert gas includes a mixture of argon and neon, and the anaesthetic agent is nitrous oxide. The inhalant is used to produce a feeling of well-being and may be inhaled at predetermined intervals over a predetermined time period. The inhalant may also be used to assist in smoking cessation by being used when a desire for a cigarette is experienced. Uses are also contemplated for deep-sea divers and athletes in training.

3 Claims, No Drawings

INHALANT FOR REDUCING STRESS AND METHOD OF USE

BACKGROUND OF THE INVENTION

1. Field of the Invention

The present invention relates to relaxation-producing substances, and, more particularly, to inhalants for producing a feeling of relaxation or a reduction of stress and methods of using same.

2. Description of Related Art

The use of inhalants for the purpose of anaesthesia has been known for over 100 years. For example, Barker (U.S. Pat. No. 87,319) mentions the use of nitrous oxide with chloroform or other anaesthetic agents to produce anaesthesia. Mayo (U.S. Pat. Nos. 283,800 and 320,150) and Bracken and Wilton-Davies (U.S. Pat. No. 3,192,106 and G. B. Pat. No. 967,930) disclose a combination of nitrous oxide with other ingredients to achieve anaesthesia.

SUMMARY OF THE INVENTION

It is an object of the present invention to provide an inhalant composition and method of use for achieving a reduction of perceived stress in a human.

It is another object to provide such a composition and method of use for achieving an elevated mood.

It is yet another object to provide such a composition and method of use for alleviating the effects of air pollution.

It is an additional object to provide such a composition and method of use that assists in smoking cessation.

It is a further object to provide such a composition and method of use that is useful following deep-sea diving.

These and other objects are attained by the inhalant composition and method of use of the present invention. The inhalant, which is for reducing a feeling of stress in a human, has a composition comprising nitrogen, sufficient oxygen to preclude asphyxia, an inert gas, and an anaesthetic agent present in a proportion insufficient to produce anaesthesia.

In a preferred embodiment of the inhalant, the inert gas comprises at least one of the group consisting of argon, neon, helium, krypton, and xenon. In a most preferred embodiment, the inert gas comprises neon and argon.

Also in a preferred embodiment, the anaesthetic agent comprises nitrous oxide.

In the method of the present invention, a feeling of well-being is achieved by inhaling the above-recited inhalant at predetermined intervals over a predetermined time period.

In another embodiment of the present invention, the above-recited inhalant may be inhaled at predetermined intervals to assist in the cessation of cigarette smoking. Preferably the inhalant is used when an urge to smoke a cigarette is experienced, or when such an urge is anticipated.

In yet another embodiment of the present invention, the above-recited inhalant may be utilized by athletes after periods of heavy training to assist in postexertion relaxation and also by deep-sea divers following a dive to alleviate the effects of a high-pressure environment.

In a further embodiment, the inhalant may be administered to a mammal preparatory to a potentially stressful experience, such as being crated and moved.

The features that characterize the invention, both as to organization and method of operation, together with further objects and advantages thereof, will be better understood from the following description. These and other objects attained, and advantages offered, by the present invention will become more fully apparent as the description that now follows is read.

DETAILED DESCRIPTION OF THE PREFERRED EMBODIMENTS

A description of the preferred embodiments of the present invention will now be presented.

A first embodiment of the invention is an inhalant composition for reducing a feeling of stress in a mammal. Broadly, the composition comprises nitrogen and sufficient oxygen to preclude asphyxia, generally in the range above 20 vol % and preferably below 60 vol %, where it becomes toxic. The composition also comprises an inert gas and an anaesthetic agent present in a proportion insufficient to produce anaesthesia.

In a preferred embodiment, the inert gas comprises at least one of the group consisting of argon, neon, helium, krypton, and xenon; that is, any of the inert gases may be used except radon. Preferably, although not intended to be limiting, the inert gas comprises neon and argon present in the approximate ranges of 7.0–9.0 and 2.8–3.5 vol %, respectively.

In an alternate embodiment, a chlorofluorocarbon such as carbon tetrafluoride could be used.

Also in a preferred embodiment, the anaesthetic agent comprises nitrous oxide, preferably present in the approximate range of 1–5 vol %. Amounts in the range of 50 vol % are known to induce analgesia.

In an alternate embodiment, the anaesthetic agent comprises isofluorine, a mixture of nitrous oxide and isofluorine, or another nontoxic anaesthetic agent, for example, cyclopropane.

In a preferred embodiment, the composition comprises 21–40 vol % oxygen, 0–20 vol % neon, 0–60 vol % argon, 0–30 vol % nitrous oxide, 0–1.5 vol % carbon dioxide, and sufficient nitrogen to balance the inhalant to 100 vol %. In a most preferred embodiment, the composition comprises 58.6 vol % nitrogen, 28 vol % oxygen, 8.1 vol % neon, 3.2 vol % argon, 0.5 vol % carbon dioxide, and 1.5 vol % nitrous oxide, although these proportions are not intended to be limiting, and it may be contemplated within the spirit of the invention that departures may be made from these proportions to fine-tune the effect of the inhalant to the user.

The composition of the present invention has been found to induce a feeling of well-being without intoxication. The inhalant may be packaged, for example, in a pressurized tank, or in small pressurized containers for portable personal use.

The method of the present invention comprises the steps of providing the inhalant as recited above and inhaling the inhalant at predetermined intervals over a predetermined time period to produce a feeling of well-being. Exemplary frequency and duration values may comprise, for example, 1–10 minutes twice per day, although, again, these values may be adjusted to maximize the benefit to the user.

In another embodiment of the invention, the inhalant composition may be used in concert with a cigarette smoking cessation program. In this embodiment the inhalant is used whenever the user has an urge for a cigarette. It has been found that utilizing the inhalant of the present invention reduces the perceived need for a cigarette and replaces the need with a temporary feeling of well-being and relaxation.

In other embodiments, the inhalant may be used following a deep-sea dive or following an airplane flight to alleviate the negative effects of ambient pressure differentials, or during childbirth to induce relaxation.

It should be noted that the inert gas and/or anaesthetic agent, both the type and the proportion, may be tailored for each specific application and for each specific user, and that, within the exemplary ranges given, flexibility is an important feature of the invention.

It may be appreciated by one skilled in the art that additional embodiments may be contemplated, including alternate combinations of ingredients to produce a similar inhalant, as well as related methods of using such a composition.

In the foregoing description, certain terms have been used for brevity, clarity, and understanding, but no unnecessary limitations are to be implied therefrom beyond the requirements of the prior art, because such words are used for description purposes herein and are intended to be broadly construed. Moreover, the embodiments of the composition and method described herein are by way of example, and the scope of the invention is not limited to the exact details of the composition and method of use.

Having now described the invention, the composition and the use of preferred embodiments thereof, and the advantageous new and useful results obtained thereby, the new and useful compositions and reasonable chemical equivalents thereof obvious to those skilled in the art, are set forth in the appended claims.

What is claimed is:

1. An inhalant composition for reducing a feeling of stress in a mammal, the composition comprising nitrogen, sufficient oxygen to preclude asphyxia, an inert gas, and an anaesthetic agent present in a proportion insufficient to produce anaesthesia, wherein the inert gas comprises neon and argon present in approximate ranges of 1.0–9.0 vol % neon and 1.0–3.5 vol % argon.

2. The inhalant composition recited in claim 1, wherein the anaesthetic agent comprises nitrous oxides present in an approximate range of 1–10 volume percent.

3. An inhalant composition for reducing a feeling of stress in a mammal, the composition comprising 58.6 volume percent nitrogen, 28 volume percent oxygen, 8.1 volume percent neon, 3.2 volume percent argon, 0.5 volume percent carbon dioxide, and 1.5 volume percent nitrous oxide.

* * * * *